(12) United States Patent
Radford et al.

(10) Patent No.: US 8,602,048 B2
(45) Date of Patent: Dec. 10, 2013

(54) APPARATUS AND INSTRUMENTS FOR HANDLING GAS AND INCORPORATING A SAFETY VALVE UNIT

(75) Inventors: Richard Radford, Neward (GB); David Edgar Peel, Southwell (GB)

(73) Assignee: BPR Medical Limited, Nottinghamshire (GB)

( * ) Notice: Subject to any disclaimer, the term of this patent is extended or adjusted under 35 U.S.C. 154(b) by 1180 days.

(21) Appl. No.: 12/456,689

(22) Filed: Jun. 18, 2009

(65) Prior Publication Data

US 2009/0288662 A1 Nov. 26, 2009

(30) Foreign Application Priority Data

Dec. 21, 2006 (GB) .................................. 0625585.5
May 21, 2007 (GB) .................................. 0709683.7
Dec. 19, 2007 (WO) ................ PCT/GB2007/004872

(51) Int. Cl.
*F16K 17/14* (2006.01)

(52) U.S. Cl.
USPC ................................ 137/75; 137/72; 137/468

(58) Field of Classification Search
USPC ........................ 137/72–77, 457, 468; 169/69; 251/89–116
See application file for complete search history.

(56) References Cited

U.S. PATENT DOCUMENTS

| | | | |
|---|---|---|---|
| 4,143,670 A * | 3/1979 | Olson et al. ...................... | 137/72 |
| 4,235,267 A | 11/1980 | Brake et al. | |
| 4,479,520 A | 10/1984 | Holben | |
| 4,586,634 A | 5/1986 | Minter et al. | |
| 5,290,009 A | 3/1994 | Heilmann | |
| 5,392,825 A * | 2/1995 | Mims et al. ................ | 137/614.2 |
| 5,445,358 A | 8/1995 | Anderson | |
| 5,676,721 A * | 10/1997 | Fredholm et al. ................. | 65/68 |
| 5,927,312 A | 7/1999 | Dryden et al. | |
| 6,615,860 B2 * | 9/2003 | Didone et al. .................. | 137/75 |
| 2005/0253105 A1 | 11/2005 | Gardner, Jr. et al. | |

FOREIGN PATENT DOCUMENTS

| | | |
|---|---|---|
| EP | 0 930 454 | 7/1999 |
| EP | 1 455 131 | 9/2004 |
| FR | 2 724 709 | 3/1996 |
| GB | 1 047 122 | 11/1966 |
| GB | 2 111 154 | 6/1983 |
| GB | 2 417 425 | 3/2006 |
| GB | 2 418 239 | 3/2006 |
| GB | 2 425 339 | 10/2009 |
| JP | 2000120964 | 4/2000 |
| WO | WO 86/01871 | 3/1986 |

* cited by examiner

*Primary Examiner* — Lynne Anderson
(74) *Attorney, Agent, or Firm* — Weide & Miller, Ltd.

(57) ABSTRACT

Apparatus for use in delivery of gas capable of combustion that incorporates a safety valve unit. The safety valve unit closes the flow path of the gas from the source upon occurrence of a fire. The safety valve unit has a valve body, a valve head resiliently biased towards a valve-closure position and a fusible retainer that holds the valve member in a valve open position. The valve body defines a fluid flow passage between an outlet and the valve head. Within the fluid flow passage there is an elongate link member which extends from the valve head to the foot. The foot engages the fusible retainer.

9 Claims, 8 Drawing Sheets

APPARATUS AND INSTRUMENTS FOR HANDLING GAS AND INCORPORATING A SAFETY VALVE UNIT

CROSS-REFERENCE TO RELATED APPLICATIONS

This application claims priority to PCT Application No. PCT/GB2007/004872 titled Apparatus and Instruments for Handling Gas and Incorporating a Safety Valve Unit, filed Dec. 19, 2007 which claims priority to Great Britain Application No. 0709683.7 filed May 21, 2007, which claims priority to Great Britain Application No. 0625585.5 filed Dec. 21, 2006.

FIELD OF THE INVENTION

The invention relates to gas handling and distribution and in particular to a gas handling apparatus incorporating a safety valve.

RELATED ART

Disclosed herein is an apparatus and instrument for handling gas capable of combustion or of supporting combustion, and incorporating a safety valve unit and is specifically, but not exclusively, concerned with such apparatus and instruments as are used in association with respirators for supplying oxygen to patients both in hospitals, by emergency services, and more particularly in the domestic environment where awareness of the danger resulting from the use of an oxygen enriched environment may not be so readily appreciated.

The provision of supplementary oxygen for patients suffering from acute respiratory disorders is becoming more widespread. The delivery of such oxygen to the patient is usually effected by an interface such as a nasal cannula, a face mask or even an endotracheal tube. The oxygen is supplied to the interface unit by flexible plastic tubing from a source of oxygen.

Oxygen may be supplied in one of three ways, namely in compressed form in cylinders, from concentrators which extract oxygen from the atmosphere, or as liquid oxygen in a Dewar flask. Such sources are coupled typically via a plastic line to a face mask, nasal cannula or endotracheal tube.

Clinical experience, and experience in the home has established that the risk of fire when using such oxygen delivery apparatus is particularly significant since the exposure of the apparatus to a combustion igniting event such as an electrical short circuit, a faulty cooking element, open flames such as candles, matches or cigarettes can result in ignition with a flame starting as an external fire supported by oxygen leaking from the delivery apparatus, and then moving to the interior of the tubing and migrating rapidly upstream towards the oxygen source. The fire hazard resulting from the use of oxygen delivery apparatus is exacerbated in the domestic environment, where such therapy is ever more frequently utilised, because the use of the oxygen is not supervised by health care workers, and even the presence of mandatory smoke detectors, fire alarms and other such safety equipment, cannot mitigate the risks due to the rapidity of conflagration once triggered. The risk of catastrophic fires, especially due to careless use of such apparatus, is very much higher in the case of patients who smoke since there is a temptation for the patient to discard the oxygen delivery mask or cannula, leaving it lying in the vicinity, whilst a cigarette is smoked. Most oxygen delivery apparatus is set to deliver oxygen continuously at a rate determined by the needs of the patient, and removal of the delivery interface from the patient's airways does not cause the delivery of oxygen to cease. In such circumstances an oxygen-enriched atmosphere can build up around the patient, investing any bedding or furnishing materials, and preparing the environment for a catastrophic conflagration upon ignition by even the smallest spark.

There is therefore a need for apparatus and/or procedures to prevent or avoid fire occurring as a result of material ignited in an oxygen-enriched environment, in the proximity of the patient using such a respirator.

Further, the patient interface component of respiratory equipment such as facemasks and nasal cannulas are usually disposable and therefore there is a great incentive for any safety equipment associated with it to be inexpensive and easy to install. There is also a requirement for any safety valve units to be so formed that they do not weigh down on a supply line and pull on connections causing them to become loose, and also so that that a safety valve unit connected close to a mask or nasal cannula does not cause the patient undue discomfort due to its weight. Although it is known to provide safety valves for inserting in a gas delivery line, the present invention seeks to address the problem by devising a way in which a safety valve can be effectively and easily incorporated into a component of the system whilst remaining accessible for checking and easy replaceability.

SUMMARY

According to the present invention there is provided apparatus for use in delivering a gas capable of combustion or of supporting combustion incorporating a safety valve unit for closing the flow path of the gas from the source thereof upon the occurrence of a fire.

In a preferred embodiment of the invention, the safety valve unit is formed as a removable assembly having a connector nozzle by which the apparatus is connectable to the gas delivery line thereof.

Likewise it is preferred that the safety valve unit is removably connectable to the body of a component of the gas delivery apparatus or an ancillary unit associated therewith and connected in line with the gas delivery path of the apparatus. The said component part or ancillary unit may be, for example, a gas flow meter, a flow or pressure regulator, a patient interface (in the case of oxygen delivery respiratory support apparatus).

The safety valve unit itself may comprise a valve body, a valve member having a valve head resiliently biased towards a valve-closure position and a fusible retainer holding the valve member, against the bias, in a valve-open position, the valve body defining a fluid flow passage, between an outlet and the said valve head, within which is an elongate link member extending from the valve head to a foot, which engages the fusible retainer.

The elongate link member may be a generally laminar or flat element. Alternatively the elongate member may take the form of a substantially cylindrical element or a tapered cylindrical element. The elongate link member may be integral with the valve head or, alternatively, may be a separate element.

The valve head may further include a sealing member. The sealing member and the valve head may be arranged to co-operate such that the sealing member seals against the wall of the fluid flow passage when the valve member is in the closure position. The sealing member may take, for example, the form of a substantially spherical ball element, and the valve head may be shaped to seat the sealing member.

Alternatively, the valve head may have an annular recess and an annular sealing member disposed therein to form a seal between the valve head and the wall of the fluid flow passage when the valve member is in the valve closure position.

At least a portion of the surface of the valve head may be formed of a suitable material, to form a seal between the valve head and the wall of the fluid flow passage when the valve member is in the valve closure position. The whole of the head itself may be formed from such a material. Alternatively, the sealing member may be formed of a suitable material for form a seal against the wall of the fluid flow passage when the valve member is in the valve closure position.

The foot may comprise at least one lateral protrusion. However, the foot may comprise two or more lateral protrusions, which are preferably diametrically opposed across a plane of symmetry of the elongate link member.

The fusible retainer may be in the form of an inwardly directed annular flange arranged to retain the foot of the valve member within the hollow body. The fusible retainer may be formed from heat susceptible material, which may be selected from thermoplastic materials, solder and waxes. In a preferred embodiment the fusible retainer is formed from a thermoplastic material, such as, for example, polyvinylchloride (PVC).

The valve member may be resiliently-biased by a coiled compression spring mounted within the hollow body and compressed between an internal annular rim provided by the valve body and an annular shoulder of the valve head.

In another aspect, the present invention provides apparatus in which the foot comprises at least one lateral protrusion.

Valves according to the present invention may be adapted to connect directly to a component part of or ancillary unit associated with the gas delivery apparatus. The safety valve unit may, for example, be directly connectable to a Flowmeter.

In such valves the means for securing the body of the valve to a component part of or ancillary unit associated with the gas delivery apparatus comprises a hollow tubular spigot for introduction into an opening in the body of the said component or ancillary unit, gas-tight sealing means on the said spigot and means for retaining the spigot in position within the opening in the said body. The said means for retaining may comprise one or more lateral projections for forming a bayonet type coupling. Alternatively, the said means for retaining comprises a screw threaded portion for engaging a corresponding screw thread in the opening.

The present invention also encompasses a respiratory support apparatus incorporating such a safety valve.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views. By way of example only, embodiments of the present invention are described in relation to the accompanying drawings, in which.

DETAILED DESCRIPTION

Figure 1:
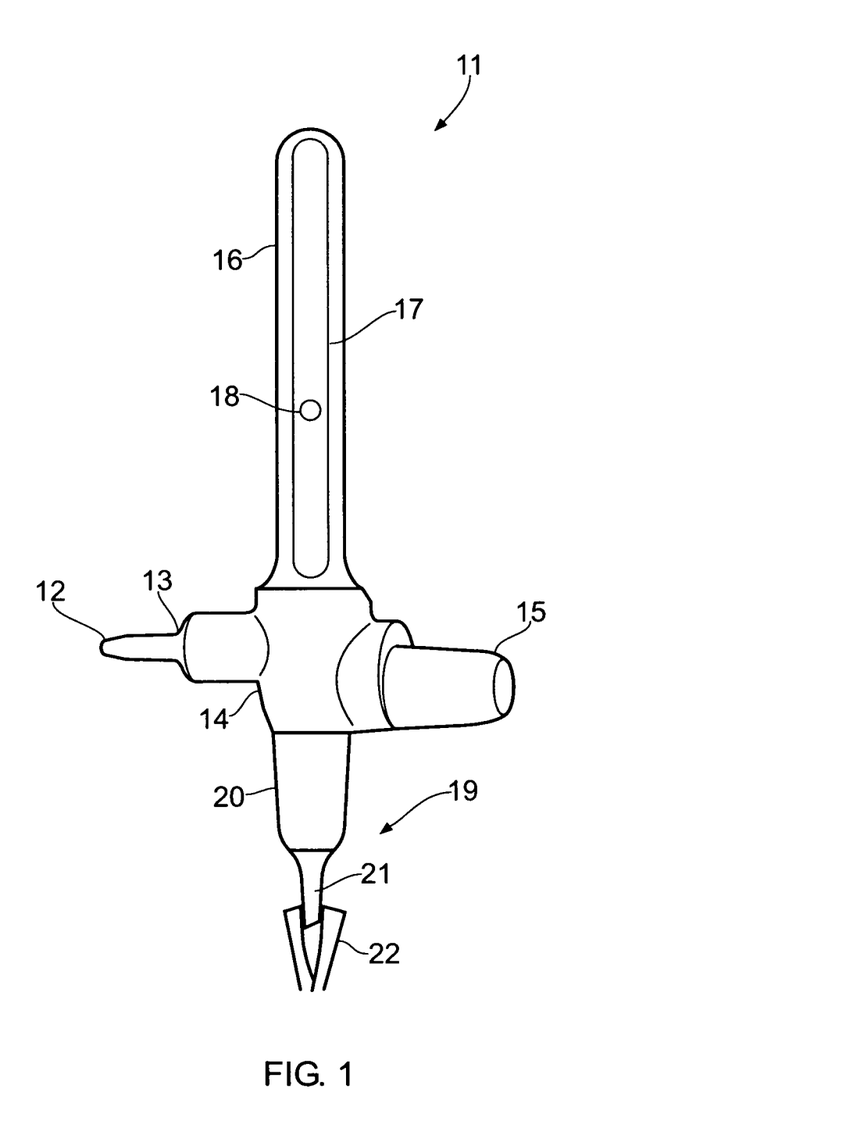
FIG. 1 is a front view of a flowmeter incorporating a safety valve unit in accordance with the present invention.

Referring now to the drawings and particularly to FIG. 1, there is shown a flowmeter generally indicated 11, intended to form part of gas delivery apparatus adapted as respiratory support system for delivering oxygen from a source (not shown) which is connected by a flexible line generally indicated 12 to an inlet nozzle 13 projecting from a generally cylindrical body 14 of the flowmeter.

From the body 14 of the flowmeter projects a control knob 15 which is turnable to control the rate of flow of gas through the unit. Projecting upwardly from the body 14 is a hollow, cylindrical flow-indicator body 16 having a transparent window 17 through which the interior passage of the indicator body 16 can be observed. Within this passage is located a lightweight ball generally indicated 18. In use of the flow indicator gas arriving at the inlet 13 is passed up the interior passage 17 within the indicator body 16, carrying with it the lightweight ball 18. The gas is then passed down a passage (not shown) back to the body 14 from where it exits through an outlet generally indicated 19. The outlet 19 is formed as a safety valve 20 having an outlet nozzle 21 to which can be connected a flexible line generally indicated 22 leading to the delivery outlet of the gas delivery apparatus, which may, in the case of respiratory support apparatus, be a nasal cannula device as shown in FIG. 2, or a facemask as shown in FIG. 3.

The safety valve 20 is one having a heat-sensitive element located in the connector nozzle 21 which, should the patient initiate a fire at the delivery end of the apparatus, for example by smoking, detect the rise in temperature as the flame front approaches along the line 22 and fuse to allow a valve element within the unit 20 to close thereby isolating the flowmeter 11 and the remainder of the delivery apparatus, including, especially, the source of combustion-supporting gas (usually oxygen) from the fire.

Figure 2:
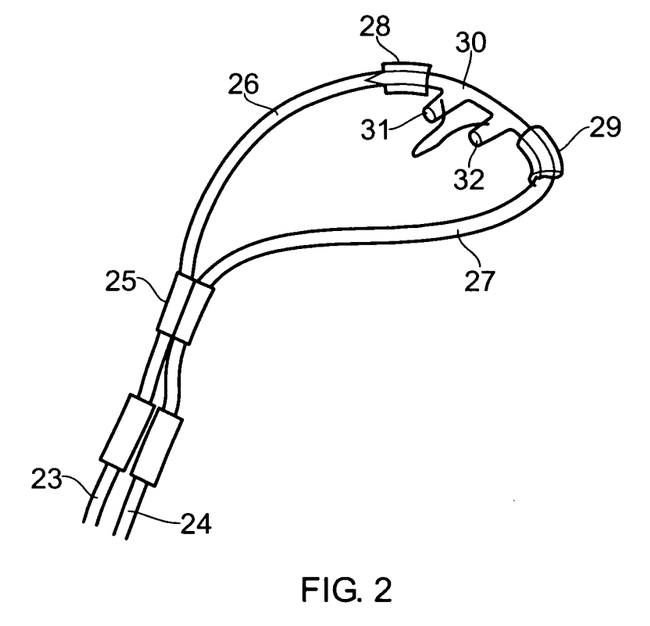
FIG. 2 is a perspective view of a nasal cannula delivery respiratory support system incorporating safety valves in accordance with the principles of the present invention.

FIG. 2 illustrates the delivery end of the apparatus a part of which is shown in FIG. 1, this comprising two parallel flexible lines 23, 24 which lead from the single line 22 (by means of a branching or twinning device (not shown)) which are held together by means of a sleeve 25. End portions 26, 27 of the lines 23, 24 are formed into a loop and connected, via respective safety valves 28, 29 to a nasal cannula 30 of known type having two parallel outlet nozzles 31, 32 which are, in use, introduced into respective nostrils of a user. The safety valves 28, 29, like the valve 20 in the embodiment of FIG. 1, act to detect a rise in temperature indicating that a fire has started, and close to isolate the remainder of the system from the source of the fire. By positioning the valves 28, 29 close to the nasal cannula 30 a rapid response to the initiation of a fire can be achieved. In an alternative embodiment, not shown, these valves may be positioned further down the lines 26, 27 or in the sections 23, 24 of the lines upstream of the sleeve 25.

Figure 3:
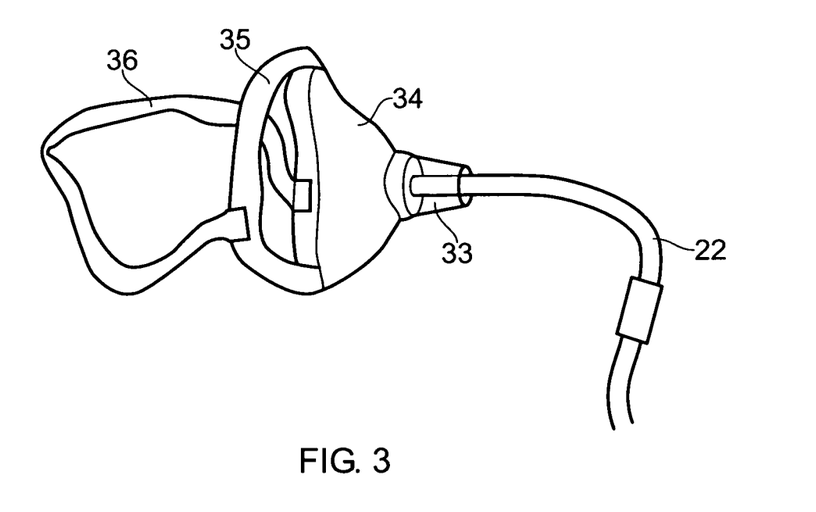
FIG. 3 is a perspective view of a face mask patient interface device for a respiratory support system incorporating a safety valve in accordance with the present invention.

In the embodiment of FIG. 3 the line 22 is shown connected by a safety valve 33 to a facemask 34 having a normal configuration with a padded rim 35 and elasticated retaining band 36.

As with the safety valves 28, 29 of the embodiment of FIG. 2, the valve 33 senses a rise in temperature indicating that a fire may have started and closes communication with the line 22. This is particularly important in circumstances where, for example, the respiratory support apparatus of which the facemask or nasal cannula (in the embodiment of FIG. 2) are used in the home without close clinical supervision since a forgetful patient may remove the mask or cannula and place it on the bed or chair next to him or her, and then engage in some activity, such as smoking, lighting candles or the like which might cause ignition of the gas leaking from the open end of the delivery apparatus. It will be appreciated that, in the majority of cases, the oxygen delivered through the line 22 is emitted at a metered rate suitable for the patient during inhalation, but continues during exhalation at the same rate so that the atmosphere around the patient becomes oxygen-enriched whilst the apparatus is in use, and, of course, should the delivery outlet be put down away from the patient, the flow of gas continues unabated unless turned off at a main control valve.

Figure 4:
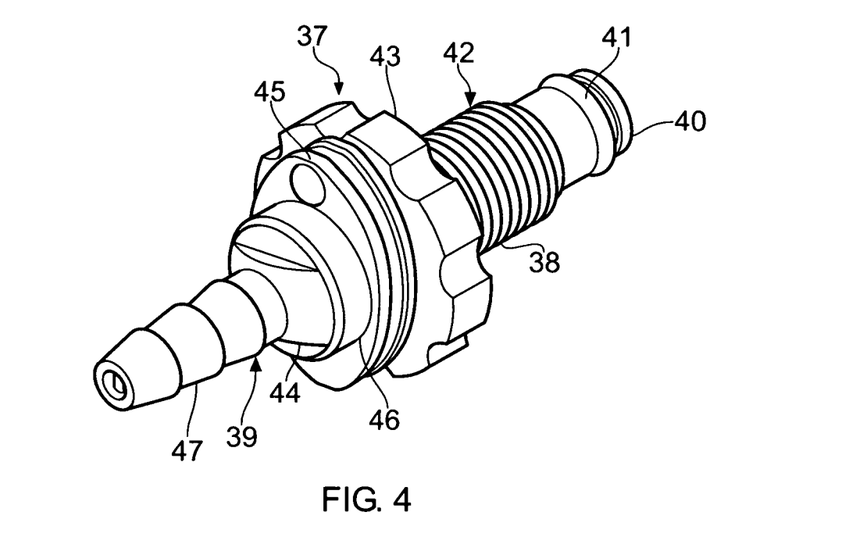
FIG. 4 is a perspective view of a safety valve in accordance with the present invention, adapted to fit onto a component part or ancillary unit of gas delivery apparatus.

The present invention also comprehends safety valves adapted to be fitted directly to the body of a pressure regulator, flowmeter or other item of a gas delivery system. In the embodiment of FIG. 4, a safety valve, generally indicated 37 is formed in two parts, 38, 39 which can be fitted together, for example, by screwing. The part 38 comprises substantially a hollow cylindrical spigot having an open or mouth end 40 with a circumferential annular groove in its vicinity, housing an o-ring seal 41. A major portion 42 is threaded, and a radial hand grip 43 is provided at the end remote from the mouth 40 to assist not only in securing the safety valve 37 in position on the component to which it is intended to be fitted, but also to assist in connecting the second component 39 thereto. This second component 39 comprises a generally cylindrical body portion 44 with two opposite radially projecting luggs 45, 46 serving as hand grips, and having a hollow nozzle 47 in axial alignment with the hollow spigot. A typical interior construction of the safety valve will be described in more detail in relation to FIG. 6.

Figure 5:
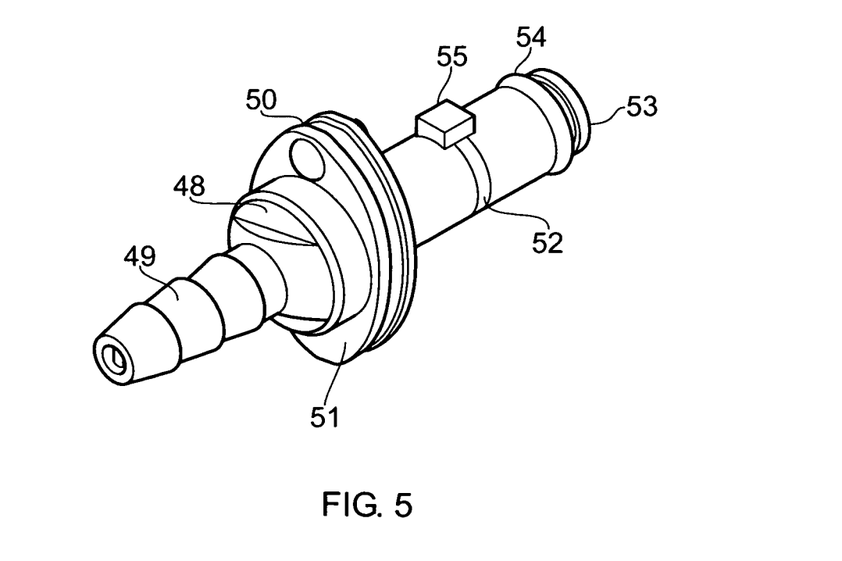
FIG. 5 is a perspective view of an alternative form of safety valve unit adapted to fit a component part or ancillary unit of gas delivery apparatus.

Turning now to FIG. 5, the further embodiment comprises a main body portion 48 from which projects a nozzle 49 corresponding in function to the nozzle 47 in the embodiment of FIG. 4.

Projecting radially from the body 48 are two radial projections 50, 51 which form part of a generally electicle enlargement of the body 48 and serve as a hand grip for fitting and removing the safety valve. Projecting axially in the opposite direction from the nozzle 49 is a hollow tubular spigot 52 which, like the embodiment of FIG. 4, has an open mouth 53 and an o-ring seal 54 housed in a circumferential annual groove adjacent to the open mouth end 53.

Projecting laterally from the cylindrical body of the spigot 52 is a radial boss 55 which, when the valve is fitted to a component in the gas delivery system, engages within an axial slot and, upon turning of the body 48 by means of the luggs 50, 51 forms a bayonet-type coupling within the apparatus.

Figure 6:
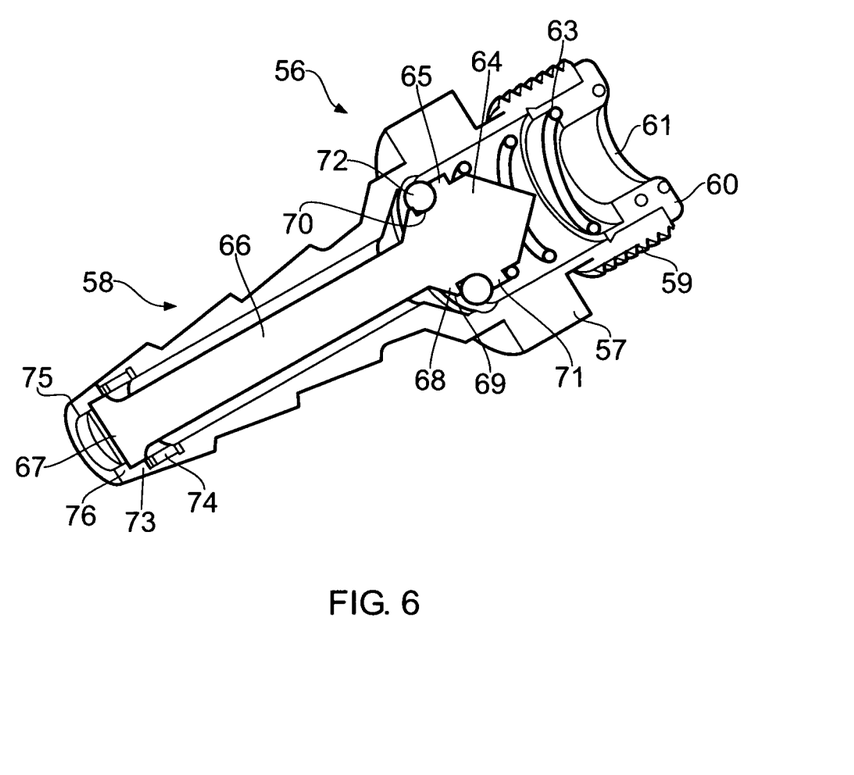
FIG. 6 is an axial section through a further safety valve unit formed in accordance with the principles of the present invention.

Turning now to FIG. 6 shows an exemplary interior structure for the safety valve. It is to be understood, however, that the interior structure of the safety valves referred to in the embodiments of FIGS. 1 to 5 may not necessarily be identical to this and that other safety valve configurations, for example that known from the applicants own earlier patent application number GB0624524.5 may be employed.

In FIG. 6 it can be seen that the valve shown has a body 56 with a cylindrical main body portion 57 from which projects a nozzle 58 in one direction and a hollow spigot 59 in the other. The open end of the spigot 59 receives an annular cap 60 with a central opening 61 which defines an annular shoulder 62 the function of which is to engage one end of a spring 63 which urges a valve shutter 64 towards a valve-closure position as will be explained in more detail below.

The opposite end of the spring 63 acts upon the valve shutter member 64 which is mounted within the valve body 57. The valve shutter member 64 comprises a head 65 integrally formed with an elongate link member 66 which extends through the nozzle 56 and terminates in a foot 67. The elongate link member 66 is generally planar while the head 65 has a conically tapering neck portion 68, shaped to correspond with an annular valve seat 69 formed on the internal surface of the body 57. The head 65 has an annular recess 70 defined between the neck portion 68 and a shoulder 71.

The end of the spring 63 bears against the shoulder 71 and the recess 70 accommodates a resilient sealing o-ring 72, the function of which is described below.

The foot 67 of the elongate link member 66 bears against a fusible retaining member in the form of a collar 73 which is mounted at the exit end of the nozzle 58. The retaining collar 73 has a sleeve portion 74 and an annular end portion 75. The sleeve portion 74 fits within the open end of the nozzle and has lugs which form a snap fit with rim recess on the inside surface of the body. The annular end portion 75 provides a radially inwardly extending shoulder or rim 76 against which the foot 67 bears.

The retaining collar 73 is formed of a material which is sensitive to heat and softens or fuses at the temperatures such as may be caused by flashback and/or ignition of a gas. At the same time, the material must have sufficient strength that, in use, it retains its structural integrity within the exit end of the nozzle section against the compressive force of the spring 63 acting thereon by way of the valve member 65, the link 66 and the foot 67. Suitable materials are some thermoplastics such as, for example, polyvinylchloride (PVC), and materials such as waxes and lead free solder.

The internal surface of the body 57 defines the annular shoulder 69 which is of generally frusto-conical form. The tapered annular shoulder is arranged to be engaged by the O-ring 72 in the event of fusing of the collar 73, due to its exposure to excessive heat, for example, due to fire or explosion in its vicinity.

In use the safety valve of the present invention is fitted between the circuit from a pressurised gas supply such as that commonly used in the home for those requiring oxygen to assist a patient's breathing, and a respiratory support device, such as a mask or nasal cannula. The gas supply may be in the form of an oxygen cylinder which provides oxygen for enrichment of normal oxygen intake by admixture with ambient air, or may be in the form of a source of oxygen-enriched air, both being under pressure. The pressure of the supply to the patient is regulated by suitable pressure regulators (not shown). The valve unit according to the invention is, in use, positioned so as to ensure that in the event of the oxygen or oxygen-enriched air igniting, this supply can be cut off quickly. To this end, if the collar 73 softens in the event of increased temperature to an extent such that it weakens sufficiently no longer to resist the force of the spring 63, the spring will overcome its resistance, thereby moving the valve member immediately to urge the sealing ring 72 against the annular shoulder 69, thereby closing the valve unit.

Figure 7:
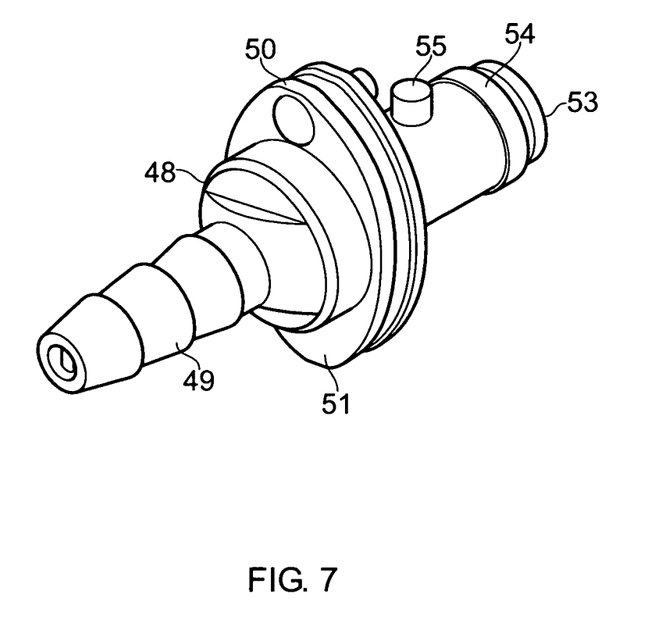
FIGS. 7, 8 and 9 are perspective views of alternative forms of safety valve unit in accordance with the present invention, adapted to fit onto a component part or ancillary unit of gas delivery apparatus.
Figure 8:
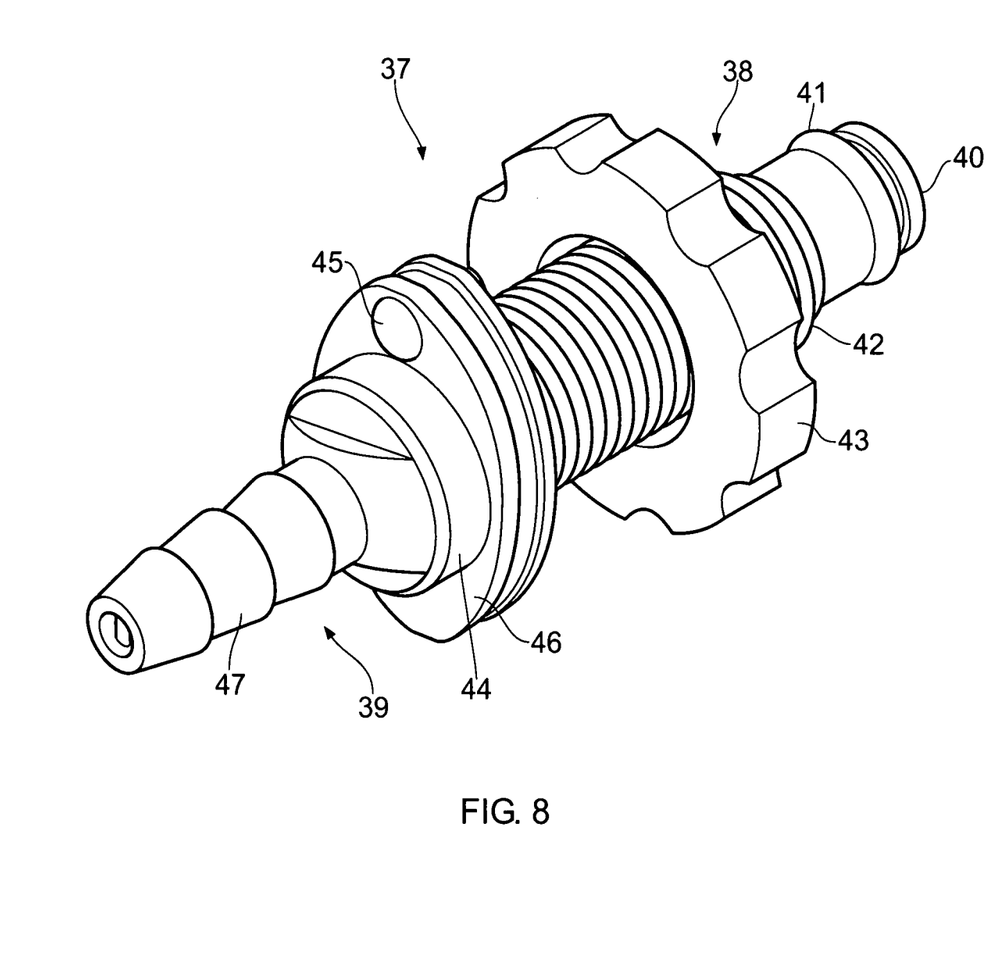
Figure 9:
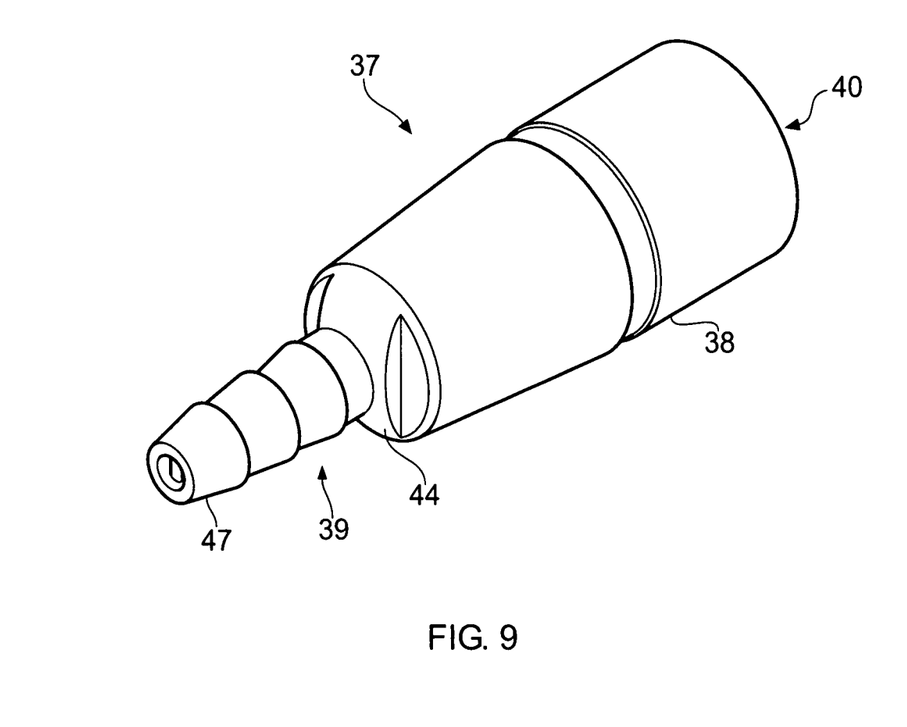

FIGS. 7, 8 and 9 share various features with the forms of safety valve unit shown in FIGS. 4 and 5. The safety valve unit of FIG. 7 is an alternative version of the safety valve unit of FIG. 5 and the safety valve unit of FIG. 8 is an alternative version of the safety valve unit of FIG. 4. The same numbering conventions have therefore been used in relation to these figures where appropriate. In the embodiment of FIG. 9, the safety valve, generally indicated 37 is formed in two parts, 38, 39 which can be fitted together, for example, by screwing. The part 38 comprises substantially a hollow cylindrical portion having an open or mouth end 40. The second component 39 comprises a generally frustroconical body portion 44 and has a hollow nozzle 47 in axial alignment with the hollow cylindrical portion 38.

Figure 10:
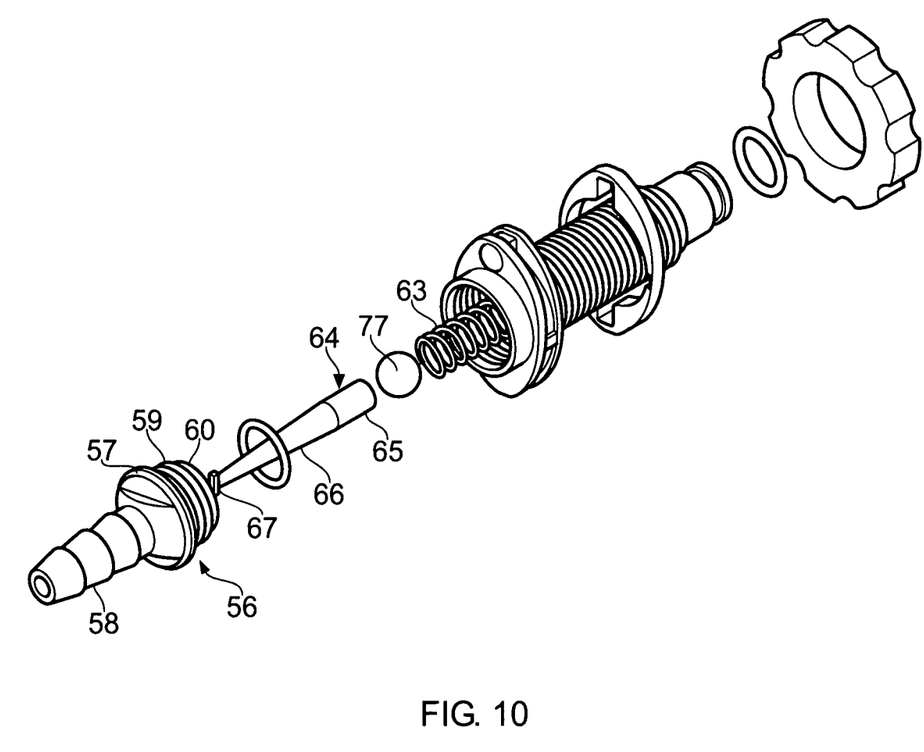
FIG. 10 is an exploded perspective view of the safety valve unit of FIG. 8.

FIG. 10 is an exploded perspective view of the safety valve unit of FIG. 8. It will be appreciated that it illustrates an alternative exemplary interior structure for the safety valve.

It can be seen in FIG. 10 that the valve shown has a body 56 with a cylindrical main body portion 57 from which projects a nozzle 58 in one direction and a hollow spigot 59 in the other. As described in relation to FIG. 6, the open end of the spigot 59 receives an annular cap 60 with a central opening which defines an annular shoulder (not shown) the function of which is to engage one end of a spring 63 which urges a valve shutter 64 towards a valve-closure position as will be explained in more detail below.

The opposite end of the spring 63 acts upon the valve shutter member 64 which is mounted within the valve body 57. The valve shutter member 64 comprises a head portion 65 integrally formed with a substantially cylindrical tapered elongate link member 66 which, in use, extends through the nozzle 56 and terminates in a foot portion 67. The elongate link member 66 is generally cylindrical and tapered. The head portion includes a cup shaped seat (not shown) formed to receive a substantially spherical ball sealing element 77.

The end of the spring 63 bears against the sealing element 77, the function of which is described below.

The foot 67 of the elongate link member 66 bears against a fusible retaining member in the form of a collar (not shown) which is mounted at the exit end of the nozzle 58. The retaining collar has a sleeve portion and an annular end portion as described in relation to FIG. 6. The sleeve portion fits within the open end of the nozzle and has lugs which form a snap fit with rim recess on the inside surface of the body. The annular end portion 75 provides a radially inwardly extending shoulder or rim against which the foot 67 bears.

The retaining collar is formed of a material which is sensitive to heat and softens or fuses at the temperatures such as may be caused by flashback and/or ignition of a gas. At the same time, the material must have sufficient strength that, in use, it retains its structural integrity within the exit end of the nozzle section against the compressive force of the spring 63 acting thereon by way of the valve member 65, the link 66 and the foot 67. Suitable materials are some thermoplastics such as, for example, polyvinylchloride (PVC), and materials such as waxes and lead free solder.

The internal surface of the body 57 defines the annular shoulder 69 which is of generally semihemispherical form. The tapered annular shoulder is arranged to be engaged by the sealing element 77 in the event of fusing of the collar, due to its exposure to excessive heat, for example, due to fire or explosion in its vicinity.

The invention claimed is:

1. A safety valve for use in a gas delivery apparatus for delivering a gas capable of combustion or of supporting combustion, the safety valve comprising:
    a body;
    a nozzle for connection to a delivery line for delivering the gas to an end utilizer; and
    means for securing the body of the safety valve to a component part of or ancillary unit associated with the gas delivery apparatus in gas communication relation therewith.

2. The safety valve as claimed in claim 1, in which the means for securing the body of the safety valve to a component part of or ancillary unit associated with the gas delivery apparatus comprises a hollow tubular spigot for introduction into an opening in a component part body or an ancillary unit body, gas-tight sealing means on the hollow tubular spigot, and means for retaining the hollow tubular spigot in position within the opening in the component part body or the ancillary unit body.

3. The safety valve as claimed in claim 2, in which the means for retaining comprises one or more lateral projections for forming a bayonet type coupling.

4. The safety valve as claimed in claim 2, in which the means for retaining comprises a screw threaded portion for engaging a corresponding screw thread in the opening.

5. The safety valve as claimed in claim 2, in which the gas-tight sealing means comprises a resilient o-ring engaged in a circumferential groove surrounding a mouth of the hollow tubular spigot.

6. The safety valve as claimed in claim 1, in which a heat sensitive fusible element is located at an exit end of the nozzle.

7. The safety valve as claimed in claim 1, in which the safety valve is held open by engagement with a heat-softenable delivery tube coupled to the nozzle.

8. A safety valve for use in medical apparatus for delivering a gas capable of combustion or of supporting combustion, the safety valve comprising a valve body that comprises:
    a nozzle, wherein the nozzle is configured for connection to a delivery line configured to deliver gas to the valve body;
    a connector for securing the valve body to a gas delivery apparatus, the gas delivery apparatus configured to deliver gas to a person; and
    a heat sensitive material configured to cease gas flow through the delivery line in response to heat.

9. The safety valve of claim 8, wherein the heat sensitive material comprises a material selected from the group consisting of: waxes, thermoplastic, solder, and polyvinylchloride.

* * * * *